United States Patent [19]

Meyer et al.

[11] 3,957,924

[45] May 18, 1976

[54] O,S-DIALKYL URIDO THIOPHOSPHATES

[75] Inventors: Willy Meyer, Basel; Beat Bohner, Binningen; Dag Dawes, Pratteln, all of Switzerland

[73] Assignee: Ciba-Geigy Corporation, Ardsley, N.Y.

[22] Filed: Sept. 30, 1974

[21] Appl. No.: 510,340

[30] Foreign Application Priority Data

Oct. 5, 1973 Switzerland.................. 14260/73
July 24, 1974 Switzerland.................. 10211/74

[52] U.S. Cl............................. 260/938; 260/207.1; 260/327 R; 260/340.3; 424/202; 424/203; 424/211
[51] Int. Cl.²...................... C07F 9/38; A01N 9/36
[58] Field of Search............................ 260/938

[56] References Cited
UNITED STATES PATENTS 3,383,194  5/1968  Young.......................... 260/938 X

*Primary Examiner*—Anton H. Sutto
*Attorney, Agent, or Firm*—Frederick H. Rabin

[57] ABSTRACT

New urea phosphonates, their manufacture and use as active ingredients in pesticides especially insecticides and acaricides is disclosed. The compounds correspond to the formula

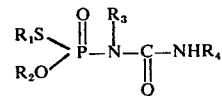

wherein $R_1$ represents $C_3$–$C_5$-alkyl, $R_2$ represents methyl or ethyl, $R_3$ represents $C_1$–$C_4$-alkyl or $C_3$–$C_4$-alkenyl, and $R_4$ represents optionally substituted phenyl.

37 Claims, No Drawings

O,S-DIALKYL URIDO THIOPHOSPHATES

The present invention relates to urea phosphonates, to processes for their preparation and to their use in pest control.

The said urea phosphonates correspond to the formula

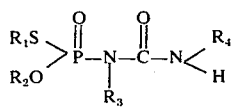

(I)

wherein
- $R_1$ represents $C_3$–$C_5$-alkyl,
- $R_2$ represents methyl or ethyl,
- $R_3$ represents $C_1$–$C_4$-alkyl or $C_3$–$C_4$-alkenyl, and
- $R_4$ represents optionally substituted phenyl.

The alkyl and alkenyl groups denoted by $R_1$ and $R_3$ can be straight-chain or branched-chain, unsubstituted, or substituted by, for example, halogen such as fluorine, chlorine, bromine and/or iodine, $C_1$–$C_4$-alkoxy or $C_1$–$C_4$-alkylthio. Examples of such groups are, inter alia: methyl, methoxymethyl, methylthiomethyl, ethyl, chloroethyl, propyl, isopropyl, n-, i-, sec.-, tert.-butyl, n-pentyl and isomers thereof, allyl and 2-methallyl.

Preferred substituents on the phenyl group are, inter alia: halogen, preferably fluorine, chlorine and/or bromine, $C_1$–$C_4$-alkyl, $C_1$–$C_4$-haloalkyl, especially -$CF_3$, $C_1$–$C_4$-alkoxy, $C_1$–$C_4$-alkylthio, $C_1$–$C_2$-alkylsulphinyl, $C_1$–$C_2$-alkylsulphonyl, $C_1$–$C_4$-alkoxycarbonyl, $C_3$–$C_4$-alkenyloxy, $C_3$–$C_4$-alkynyloxy, cyano, $C_3$–$C_4$-alkenyl, acetyl, acetylamino, aminocarbonyl optionally substituted with $C_1$–$C_4$-alkyl groups, -$OCH_2$-$CH_2$-O-,

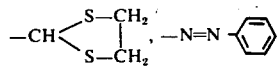

and/or nitro.

Compounds of formula I which are of importance by virtue of their action are those wherein
- $R_1$ represents unsubstituted, straight-chain or branched-chain $C_3$–$C_5$-alkyl,
- $R_2$ represents methyl or ethyl,
- $R_3$ represents straight-chain or branched-chain unsubstituted $C_1$–$C_4$-alkyl or $C_3$–$C_4$-alkenyl, and
- $R_4$ represents unsubstituted phenyl, or phenyl mono- or poly-substituted, identically or differently, by $C_1$–$C_5$-alkyl, $C_1$–$C_5$-alkoxy, $C_1$–$C_5$-alkylthio, $C_1$–$C_5$-alkyl-sulphinyl, $C_1$–$C_5$-alkylsulphonyl, halogen-$C_1$–$C_4$-alkyl, halogen, $C_3$–$C_5$-alkenyl, nitro, propargyloxy, $C_1$–$C_4$-alkoxycarbonyl, phenylazo, cyano, acetyl, acetylamino, amino-, mono-$C_1$–$C_4$-alkylamino- or di-$C_1$–$C_4$-alkylaminocarbonyl.

Particularly preferred, however, are compounds of formula I wherein
- $R_1$ represents n-propyl or sec.-butyl,
- $R_2$ represents methyl or ethyl,
- $R_3$ represents methyl, ethyl or allyl, and
- $R_4$ represents unsubstituted phenyl, or phenyl mono- or polysubstituted, identically or differently, by methyl, methoxy, methylthio, trifluoromethyl, chlorine, bromine, nitro, ethoxycarbonyl and/or acetylamino.

The compounds of formula I can be prepared by methods known per se; for example, they can be obtained as follows:

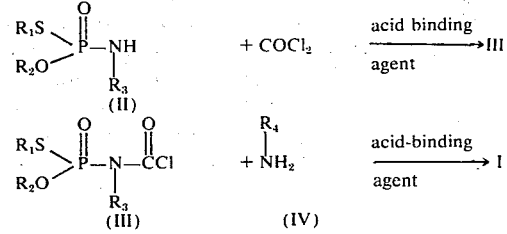

In formulae II, III and IV, the symbols $R_1$ to $R_4$ have the meanings defined for formula I.

Suitable acid-binding agents are: tertiary amines, e.g. trialkylamines, pyridine, dialkylanilines; inorganic bases such as hydrides or hydroxides, carbonates and bicarbonates of alkali metals and alkaline-earth metals. The processes are performed at a reaction temperature of $-20°$ – $150°C$, at normal pressure and in solvents or diluents. Suitable solvents or diluents are, for example, ethers and ethereal compounds such as diethyl ether, dipropyl ether, dioxane, dimethoxyethane or tetrahydrofuran; amides such as N,N-dialkylated carboxylic acid amides; aliphatic, aromatic as well as halogenated hydrocarbons, particularly benzene, toluene, xylenes, chloroform or chlorobenzene; nitriles such as acetonitrile; DMSO, ketones such as acetone or methyl ethyl ketone, and water.

The starting materials of formula II are in some cases known, and can be prepared by methods analogous, for example, to those described in the British Pat. Specification No. 1,275,330.

The active substances of formula I are suitable for the control of various animal and plant pests. They thus possess nematocidal properties and can be used, for example, for the control of phytopathogenic nematodes. In some cases, the active substances of formula I are suitable also as herbicides and as agents regulating plant growth, as well as for the control of members of the division Thallophyta, such as, for example, of viruses, bacteria and phytopathogenic fungi. They are effective in particular, however, against all development stages, sucgh as eggs, larvae, nymphs, pupae, and adults of insects and members of the order acarina, such as mites and ticks.

The compounds of formula I have a lethal or repellant action against, for example, the following insects or members of the order acarina: insects of the families: Tettigonidae, Gryllidae, Gryllotalpidae, Blattidae, Reduviidae, Phyrrhocoridae, Cimicidae, Delphacidae, Aphididae, Diaspididae, Pseudococidae, Scarabaeidae, Dermestidae, Coccinellidae, Tenebrionidae, Chrysomelidae, Bruchidae, Tineidae, Noctuidae, Lymatriidae, Pyralidae, Gulicidae, Tipulidae, Stomoxydae, Trypetidae, Muscidae, Calliphoridae and Pulicidae; as well as acarids of the families: Ixodidae, Argasidae, Tetranychidae and Dermanyssidae. The insecticidal and/or acaricidal action can be appreciably broadened and adapted to suit given circumstances by the addition of other insecticides and/or acaricides. Suitable additives are, for example: organic phosphorus compounds, nitrophenols and derivatives thereof, formamidines, ureas, pyrethrin-like derivatives, carbamates and chlorinated hydrocarbons.

Surprisingly, compounds of formula I are clearly more effective against cotton pests, such as Spodoptera littoralis and Heliothis virescens larvae $L_3$, than analogous compounds known from the U.S. Pat. No. 3,393,253.

The compounds of formula I an be used on their own or together with suitable carriers and/or additives. Suitable carriers and additives may be solid or liquid, and they correspond to the substances common in formulation practice, such as, e.g. natural or regenerated substances, solvents, dispersing agents, wetting agents, adhesives, thickeners, binders and/or fertilisers.

For application, the compounds of formula I can be processed into the form of dusts, emulsion concentrates, granulates, dispersions, sprays or solutions, the formulation of these preparations being effected in a manner commonly known in practice. Also to be mentioned are cattle dips and spray races, in which aqueous preparations are used.

The agents according to the invention are prepared in a manner known per se by the intimate mixing and/or grinding of active substances of formula I with suitable carriers, optionally with the addition of dispersing agents or solvents which are inert to the active substances. The active substances can be obtained and used in the following forms:

solid preparations:
dusts, scattering agents, granulates, coated granulates, impregnated granulates and homogeneous granulates;

liquid preparations:
a. water-dispersible active-substance concentrates: wettable powders, pastes or emulsions;
b. solutions.

The content of active substance in the above described agents is between 0.1 and 95 %.

The active substances of formula I can be formulated, for example, as follows:

Dusts:

The following substances are used in the preparation of (a) a 5% dust, and (b) a 2% dust:

a.
5 parts of active substance,
95 parts of talcum;

b.
2 parts of active substance,
1 part of highly dispersed silicic acid,
97 parts of talcum.

The active substances are mixed and ground with the carriers.

Granulate

The following substances are used to prepare a 5% granulate:
5 parts of active substance,
0.25 part of epichlorohydrin,
0.25 part of cetyl polyglycol ether,
3.50 parts of polyethylene glycol,
91 parts of kaolin (particle size 0.3 – 0.8 mm).

The active substance is mixed with epichlorohydrin and dissolved with 6 parts of acetone; the polyethylene glycol and cetyl polyglycol ether are then added. The solution thus obtained is sprayed onto kaolin, and the acetone is subsequently evaporated off in vacuo.

Wettable powder

The following constituents are used for the preparation of (a) a 40%, (b) and (c) a 25% and (d) a 10% wettable powder:

a.
40 parts of active substance,
5 parts of sodium lignin sulphonate,
1 part of sodium dibutyl-naphthalene sulphonate,
54 parts of silicic acid;

b.
25 parts of active substance,
4.5 parts of calcium lignin sulphonate,
1.9 parts of Champagne chalk/hydroxyethyl cellulose mixture (1:1),
1.5 parts of sodium dibutyl naphthalene sulphonate,
19.5 parts of silicic acid,
19.5 parts of Champagne chalk,
28.1 parts of kaolin;

c.
25 parts of active substance,
2.5 parts of isooctylphenoxy-polyoxyethylene-ethanol,
1.7 parts of Champagne chalk/hydroxyethyl cellulose mixture (1:1),
8.3 parts of sodium aluminium silicate,
16.5 parts of kieselguhr,
46 parts of kaolin;

d.
10 parts of active substance,
3 parts of a mixture of the sodium salts of saturated fatty alcohol sulphates,
5 parts of naphthalenesulphonic acid/formaldehyde condensate,
82 parts of kaolin.

The active substances are intimately mixed, in suitable mixers, with the additives, the mixture being then ground in the appropriate mills and rollers. Wettable powders are obtained which can be diluted with water to give suspensions of any desired concentration.

Emulsifiable concentrates

The following substances are used to prepare (a) a 10% and (b) a 25% emulsifiable concentrate:

a.
10 parts of active substance,
3.4 parts of epoxidised vegetable oil,
3.4 parts of a combination emulsifier consisting of fatty alcohol polyglycol ether and alkylarylsulphonate calcium salt,
40 parts of dimethylformamide,
43.2 parts of xylene;

b.
25 parts of active substance,
2.5 parts of epoxidised vegetable oil,
10 parts of an alkylarylsulphonate/fatty alcohol polyglycol ether mixture,
5 parts of dimethylformamide,
57.5 parts of xylene.

From these concentrates it is possible to prepare, by dilution with water, emulsions of any desired concentration.

Spray

The following constituents are used to prepare a 5% spray:
5 parts of active substance,
1 part of eipchlorhydrin,
94 parts of ligroin (boiling limits 160 - 190°C).

Agent for the ultra low volume spraying method 95 parts of active substance,
5 parts of epichlorhydrin.

EXAMPLE 1

Preparation of N-(propylthio-ethoxyphosphoryl)-N-methyl-carbamoyl chloride a. A mixture of 19.7 g of propylthio-ethoxyphosphoric acid-N-methylamide and 9.5 g of pyridine is added dropwise at 0°C to 11 g of phosgene in 100 ml of CCl$_4$. The suspension is afterwards stirred for 15 hours at room temperature; it is then filtered and subsequently completely concentrated by evaporation.

There is obtained the compound of the formula

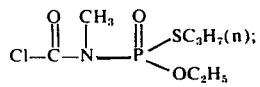

b. 22 g of N-(propylthio-ethoxyphosphoryl)-N-methylcarbamoyl chloride in 30 ml of toluene is added dropwise at room temperature to a solution of 10.9 g of p-chloroaniline and 13 ml of triethylamine in 100 ml of toluene. The suspension is stirred for 10 hours at 20°C, and then extracted by shaking with 1N hydrochloric acid, dried, and concentrated by evaporation.

There is obtained the compound of the formula

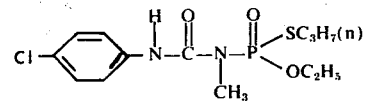

as a pale yellow liquid having a refractive index of $n_D^{20} = 1.5480$.

The following compounds are prepared in an analogous manner:

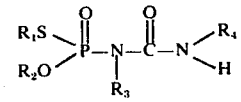

| R$_1$ | R$_2$ | R$_3$ | R$_4$ | Physical data |
|---|---|---|---|---|
| —C$_3$H$_7$(n) | —C$_2$H$_5$ | —CH$_3$ | phenyl | $n_D^{20} = 1.5395$ |
| —C$_3$H$_7$(n) | —C$_2$H$_5$ | —CH$_3$ | 2,5-dichlorophenyl | $n_D^{20} = 1.5515$ |
| —C$_3$H$_7$(n) | —C$_2$H$_5$ | —CH$_3$ | 2-CF$_3$-phenyl | $n_D^{20} = 1.5045$ |
| —C$_3$H$_7$(n) | —C$_2$H$_5$ | —CH$_3$ | 2,4-dichlorophenyl | $n_D^{20} = 1.5485$ |
| —C$_3$H$_7$(n) | —C$_2$H$_5$ | —CH$_3$ | 4-bromophenyl | $n_D^{20} = 1.555$ |
| —C$_3$H$_7$(n) | —C$_2$H$_5$ | —CH$_3$ | 2,3-dichlorophenyl | $n_D^{20} = 1.5445$ |
| —C$_3$H$_7$(n) | —C$_2$H$_5$ | —CH$_3$ | 2-fluorophenyl | $n_D^{20} = 1.5285$ |
| —C$_3$H$_7$(n) | —C$_2$H$_5$ | —CH$_3$ | 2-Cl-4-CF$_3$-phenyl | $n_D^{20} = 1.5178$ |
| —C$_3$H$_7$(n) | —C$_2$H$_5$ | —CH$_3$ | 4-Cl-2-CH$_3$-phenyl | $n_D^{20} = 1.546$ |

-continued
| R₁ | R₂ | R₃ | R₄ | Physical data |
|---|---|---|---|---|
| —C₃H₇(n) | —C₂H₅ | —CH₃ | 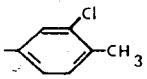 | $n_D^{20} = 1.546$ |
| —C₃H₇(n) | —C₂H₅ | —CH₃ | 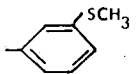 | $n_D^{20} = 1.5675$ |
| —C₃H₇(n) | —C₂H₅ | —CH₃ | 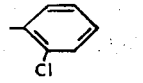 | $n_D^{20} = 1.5465$ |
| —C₃H₇(n) | —C₂H₅ | —CH₃ | 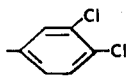 | $n_D^{20} = 1.558$ |
| —C₃H₇(n) | —C₂H₅ | —CH₃ | 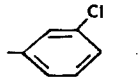 | $n_D^{20} = 1.5462$ |
| —C₃H₇(n) | —C₂H₅ | —CH₃ |  | $n_D^{20} = 1.5412$ |
| —C₃H₇(n) | —C₂H₅ | —CH₃ | 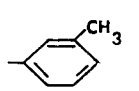 | $n_D^{20} = 1.5398$ |
| —C₃H₇(n) | —C₂H₅ | —CH₃ | 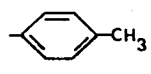 | $n_D^{20} = 1.5395$ |
| —C₃H₇(i) | —C₂H₅ | —CH₃ | 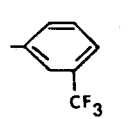 | $n_D^{20} = 1.497$ |
| —C₃H₇(n) | —C₂H₅ | —CH₃ |  | $n_D^{20} = 1.5459$ |
| —C₃H₇(n) | —C₂H₅ | —CH₃ | 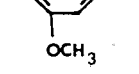 | $n_D^{20} = 1.5397$ |
| —C₃H₇(n) | —C₂H₅ | —CH₃ | 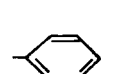 | $n_D^{20} = 1.5439$ |
| —C₃H₇(n) | —C₂H₅ | —CH₃ | 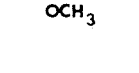 | $n_D^{23} = 1.5542$ |
| —C₃H₇(n) | —C₂H₅ | —CH₃ | 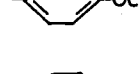 | $n_D^{23} = 1.5433$ |
| —C₄H₉(n) | —C₂H₅ | —CH₃ | 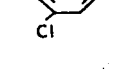 | $n_D^{24} = 1.4970$ |

-continued

| R₁ | R₂ | R₃ | R₄ | Physical data |
|---|---|---|---|---|
| —C₃H₇(n) | —C₂H₅ | —CH₃ | 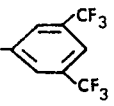 3,4-bis(CF₃)phenyl | $n_D^{23} = 1.4746$ |
| —C₃H₇(n) | —C₂H₅ | —CH₃ | 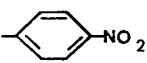 4-NO₂-phenyl | $n_D^{23} = 1.5609$ |
| —C₃H₇(n) | —CH₃ | —CH₃ |  phenyl | $n_D^{23} = 1.549$ |
| —C₄H₉(sec.) | —C₂H₅ | —CH₃ |  phenyl | $n_D^{24} = 1.5335$ |
| —C₄H₉(sec.) | —C₂H₅ | —CH₃ | 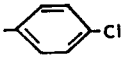 4-Cl-phenyl | $n_D^{24} = 1.542$ |
| —C₄H₉(sec.) | —C₂H₅ | —CH₃ | 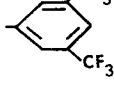 3,4-bis(CF₃)phenyl | $n_D^{24} = 1.4755$ |
| —C₃H₇(n) | —C₂H₅ | —C₂H₅ | 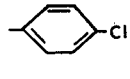 4-Cl-phenyl | $n_D^{3} = 1.554$ |
| —C₃H₇(n) | —C₂H₅ | —CH₂CH=CH₂ | 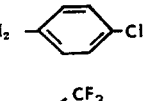 4-Cl-phenyl | $n_D^{23} = 1.547$ |
| C₃H₇(n) | C₂H₅ | —C₂H₅ | 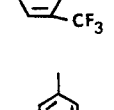 3,4-bis(CF₃)phenyl | $n_D^{23} = 1.4795$ |
| C₃H₇(n) | C₂H₅ | —C₂H₅ |  tolyl | $n_D^{23} = 1.5445$ |
| C₃H₇(n) | C₂H₅ | —C₂H₅ |  3,4-diCl-phenyl | $n_D^{23} = 1.557$ |
| —C₃H₇(n) | —C₂H₅ | —CH₃ | 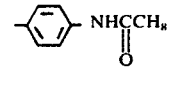 4-NHCOCH₃-phenyl | $n_D^{23} = 1.5508$ |
| —C₅H₁₁(n) | —C₂H₅ | —CH₃ |  4-Cl-phenyl | $n_D^{23} = 1.5385$ |
| —C₅H₁₁(n) | —C₂H₅ | —CH₃ | 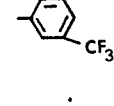 3,4-bis(CF₃)phenyl | $n_D^{23} = 1.476$ |
| —C₅H₁₁(n) | —C₂H₅ | —CH₃ |  phenyl | $n_D^{23} = 1.53$ |
| —C₃H₇(n) | —C₂H₅ | —CH₃ | 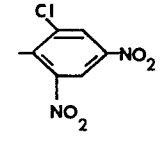 2-Cl-4,5-diNO₂-phenyl | |

| R₁ | R₂ | R₃ | R₄ | Physical data |
|---|---|---|---|---|
| —C₃H₇(n) | —C₂H₅ | —CH₃ | 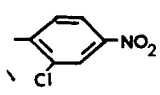 | |
| —C₃H₇(n) | —C₂H₅ | —CH₃ | 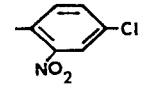 | |
| —C₃H₇(n) | —C₂H₅ | —CH₃ | 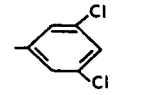 | |
| —C₃H₇(n) | —C₂H₅ | —CH₃ | 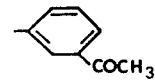 | |
| —C₃H₇(n) | —C₂H₅ | —CH₃ | 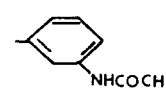 | |
| —C₃H₇(n) | —C₂H₅ | —CH₃ | 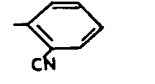 | |
| —C₃H₇(n) | —C₂H₅ | —CH₃ | 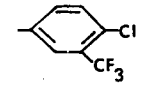 | |
| —C₃H₇(n) | —C₂H₅ | —CH₃ | 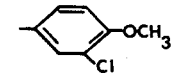 | |
| —C₃H₇(n) | —C₂H₅ | —CH₃ | 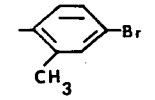 | |
| —C₃H₇(n) | —C₂H₅ | —CH₃ | 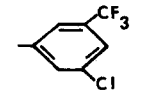 | |
| —C₃H₇(n) | —C₂H₅ | —CH₃ | 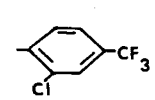 | |
| —C₃H₇(n) | —C₂H₅ | —CH₃ | 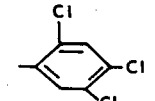 | |
| —C₃H₇(n) | —C₂H₅ | —CH₃ | 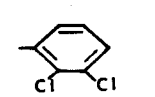 | |
| —C₃H₇(n) | —C₂H₅ | —CH₃ | 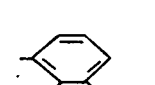 | |
| —C₃H₇(n) | —C₂H₅ | —CH₃ | 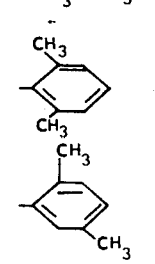 | |

-continued

| $R_1$ | $R_2$ | $R_3$ | $R_4$ | Physical data |
|---|---|---|---|---|
| $-C_3H_7(n)$ | $-C_2H_5$ | $-CH_3$ | 3-nitrophenyl | |
| $-C_3H_7(n)$ | $-C_2H_5$ | $-CH_3$ | 2-methyl-4-bromophenyl | |
| $-C_3H_7(n)$ | $-C_2H_5$ | $-CH_3$ | 4-bromophenyl | |
| $-C_3H_7(n)$ | $-C_2H_5$ | $-CH_3$ | 2-(methylthio)phenyl | |
| $-C_3H_7(n)$ | $-C_2H_5$ | $-CH_3$ | 2-ethylphenyl | |
| $-C_3H_7(n)$ | $-C_2H_5$ | $-CH_3$ | 3-nitrophenyl | |
| $-C_3H_7(n)$ | $-C_2H_5$ | $-CH_3$ | 4-chlorophenyl | |
| $-C_3H_7(n)$ | $-C_2H_5$ | $-CH_3$ | 3,5-bis(trifluoromethyl)phenyl | |
| $-C_3H_7(n)$ | $-C_2H_5$ | $-CH_3$ | 2-chloro-3-methylphenyl | |
| $(C_2H_5)_2CH-$ | $-C_2H_5$ | $-CH_3$ | 4-chlorophenyl | |
| $-C_3H_7(n)$ | $-C_2H_5$ | $-CH(CH_3)-CH=CH_2$ | phenyl | |
| $-C_3H_7(n)$ | $-C_2H_5$ | $-CH_3$ | 2-carbamoylphenyl ($-CONH_2$) | |
| $-C_3H_7(n)$ | $-C_2H_5$ | $-CH_3$ | 2-(N-methylcarbamoyl)phenyl ($-CONHCH_3$) | |

-continued

| $R_1$ | $R_2$ | $R_3$ | $R_4$ | Physical data |
|---|---|---|---|---|
| $-C_3H_7(n)$ | $-C_2H_5$ | $-CH_3$ | 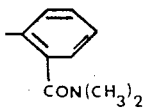 | |
| $-C_3H_7(n)$ | $-C_2H_5$ | $-CH_3$ | 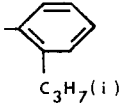 | |
| $-C_3H_7(n)$ | $-C_2H_5$ | $-CH_3$ | 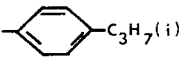 | |

EXAMPLE 2

A. Insecticidal stomach poison action

Cotton and potato plants were sprayed with a 0.05% aqueous active-substance emulsion (obtained from a 10% emulsifiable concentrate).

After the drying of the resulting coating, *Spodoptera littoralis* or *Heliothis virescens* larvae L₃ were placed onto the cotton plants, and Colorado beetle larvae (*Leptinotarsa decemlineata*) onto the potato plants. The test was carried out at 24°C with 60% relative humidity.

Compounds according to Example 1 exhibited in the above test a good insecticidal stomach poison action against Spodoptera littoralis, Heliothis virescens and Leptinotarsa decemlineata larvae.

B. Systemic insecticidal action

In order to determine the systemic action, rooted bean plants (*Vicia faba*) were placed into a 0.01% aqueous active-substance solution (obtained from a 10% emulsifiable concentrate). After a period of 24 hours, bean aphids (*Aphis fabae*) were placed onto the parts of the plant above the soil. The insects were protected by a special device from the effects of contact and of gas. The test was carried out at 24°C with 70% relative humidity.

In the above test, compounds according to Example 1 exhibited a systemic action against *Aphis fabae*.

EXAMPLE 3

Action against ticks

A. *Rhipicephalus bursa*

In each case, 5 adult ticks or 50 tick larvae were placed into a small glass test tube, and subsequently immersed for 1 to 2 minutes in 2 ml of an aqueous emulsion from a dilution series of 100, 10, 1 and 0.1 ppm of test substance. The tubes were then sealed with a standardised cotton plug, and inverted so that the active-substance emulsion could be absorbed by the cotton wool.

An evaluation in the case of the adults was made after 2 weeks, and in the case of the larvae after 2 days. There were two repeats for each test.

B. *Boophilus microplus* (larvae)

With a dilution series analogous to that in Test A, tests were carried out with 20 sensitive larvae and OP-resistant larvae, respectively (resistance is with respect to diazinon compatibility).

Compounds according to Example 1 were effective in these tests against adults and larvae and Rhipicephalus bursa and against sensitive and OP-resistant larvae, respectively, of *Boophilus microplus*.

EXAMPLE 4

Acaricidal action

*Phaseolus vulgaris* (plants) were infested, 12 hours before the test for acaricidal action, with an infested piece of leaf from a mass culture of Tetranychus urticae. The transferred mobile stages were sprayed with the emulsified test preparations from a chromatography-sprayer in a manner ensuring no running-off of the spray liquor. An assessment was made after 2 to 7 days, by examination under a binocular, of the living and of the dead larvae, adults and eggs, and the results were expressed as percentages. The treated plants were kept during the "holding time" in greenhouse compartments at 25°C.

Compounds according to Example 1 were effective in the above test against adults, larvae and eggs of Tetranychus urticae.

EXAMPLE 5

Action against soil nematodes

In order to test the action against soil nematodes, the active substances were added, in the concentration stated in each case, to soil infested with root-gall-nematodes (*Meloidogyne arenaria*); the whole was then intimately mixed. In the one test series, tomato seedlings were planted immediately after preparation of the soil in this manner, and in the other test series tomatoes were planted after a waiting time of 8 days.

For an assessment of the nematocidal action, the galls present on the roots were counted 28 days after planting and sowing, respectively.

Active substances according to Example 1 exhibited in this test a good action against *Meloidogyne arenaria*.

EXAMPLE 6

Action against *Piricularia oryzae* on *Oryzae sativa*

After being sprayed with a 0.05% suspension of the active substance made up as a wettable powder, young rice plants were, after drying of the applied coating, infested with a spore suspension of the fungus Piriarlaria orycae. After 3 days' incubation time at 24°C and with high relative humidity, an evaluation was made of the disease infestation compared with that in the case of infested but untreated control specimens. Compounds according to Example 1 were effective in this test against Piricularia oryzae.

EXAMPLE 7

Virucidal action against potato-virus Y (PVY) and cucumber mosaic virus (CMV)

Fifteen pepper plants (Capsicum annuum Var. "California Wonder") per test were cultivated in a controlled-atmosphere cupboard under well standardised conditions; and, after development of the cotyledons, transplanted to a greenhouse; they were sprayed three days later with an aqueous emulsion containing 2000 ppm of the substance to be tested and, after a further 24 hours, mechanically inoculated.

The systemic symptoms of the virus infection appeared after one week, so that it was possible to determine the antiviral activity of the tested substances.

Compounds according to Examples 1 exhibited an antiviral action against potato-virus Y and cucumber-mosaic virus on pepper plants.

We claim:
1. A compound of the formula

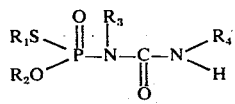

wherein
R$_1$ represents C$_3$–C$_5$ alkyl,
R$_2$ represents methyl or ethyl,
R$_3$ represents C$_1$–C$_4$ alkyl or C$_3$–C$_4$ alkenyl, and
R$_4$ represents unsubstituted phenyl, or phenyl mono- or poly-substituted, identically or differently by C$_1$–C$_3$ alkyl, methoxy, methylthio, trifluoromethyl, chlorine, bromine, nitro, ethoxycarbonyl, cyano, acetyl, acetylamino, methylaminocarbonyl or dimethylaminocarbonyl.

2. A compound according to claim 1 wherein
R$_1$ represents n-propyl or sec.-butyl,
R$_3$ represents methyl, ethyl or allyl, and
R$_4$ represents unsubstituted phenyl, or phenyl mono- or polysubstituted, identically or differently, by methyl, methoxy, methylthio, trifluoromethyl, chlorine, bromine, nitro, ethoxycarbonyl and/or acetylamino.

3. Compound according to claim 2 of the formula

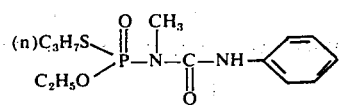

4. Compound according to claim 2 of the formula

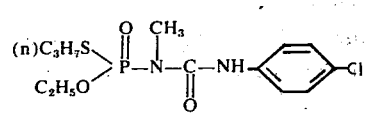

5. Compound according to claim 2 of the formula

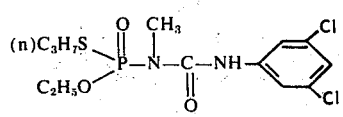

6. Compound according to claim 2 of the formula

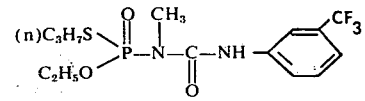

7. Compound according to claim 2 of the formula

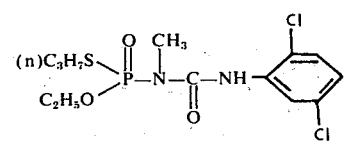

8. Compound according to claim 2 of the formula

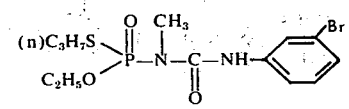

9. Compond according to claim 2 of the formula

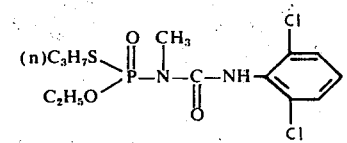

10. Compound according to claim 2 of the formula

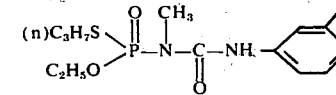

11. Compound according to claim 2 of the formula

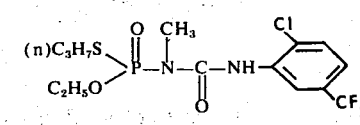

12. Compound according to claim 2 of the formula

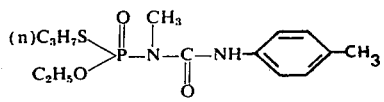

13. Compound according to claim 2 of the formula

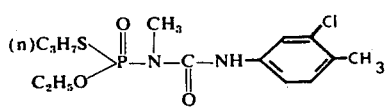

14. Compound according to claim 2 of the formula

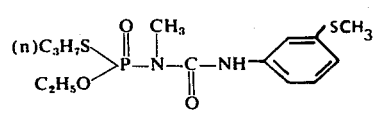

15. Compound according to claim 2 of the formula

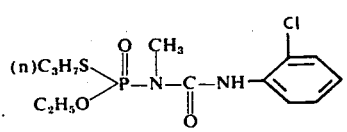

16. Compound according to claim 2 of the formula

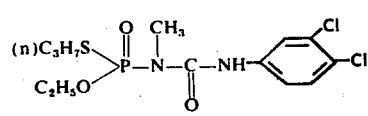

17. Compound according to claim 2 of the formula

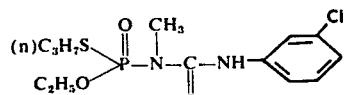

18. Compound according to claim 2 of the formula

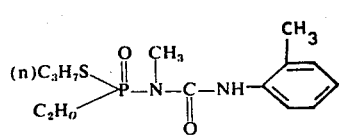

19. Compound according to claim 2 of the formula

20. Compound according to claim 2 of the formula

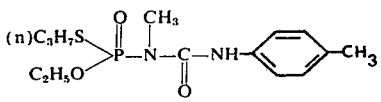

21. Compound according to claim 2 of the formula

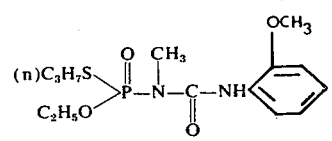

22. Compound according to claim 2 of the formula

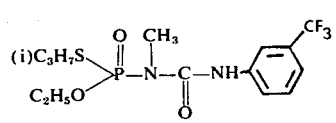

23. Compound according to claim 2 of the formula

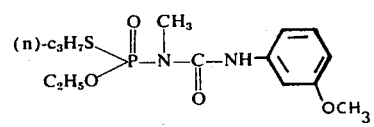

24. Compound according to claim 2 of the formula

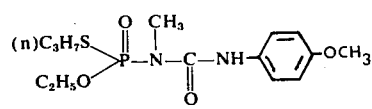

25. Compound according to claim 2 of the formula

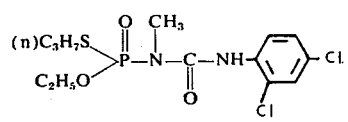

26. Compound according to claim 2 of the formula

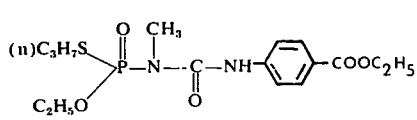

27. Compound according to claim 2 of the formula

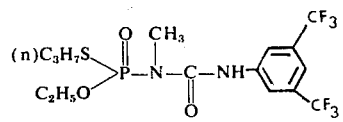

28. Compound according to claim 2 of the formula

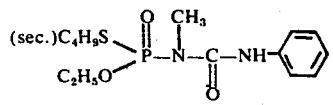

29. Compound according to claim 2 of the formula

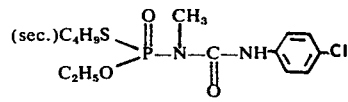

30. Compound according to claim 2 of the formula

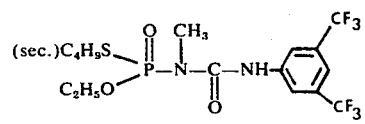

31. Compound according to claim 2 of the formula

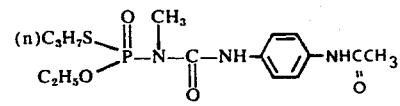

32. Compound according to claim 2 of the formula

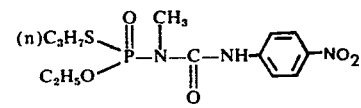

33. Compound according to claim 2 of the formula

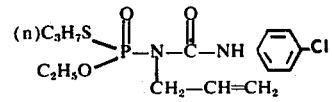

34. Compound according to claim 2 of the formula

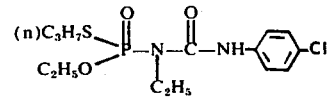

35. Compound according to claim 2 of the formula

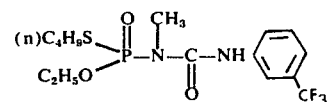

36. Compound according to claim 2 of the formula

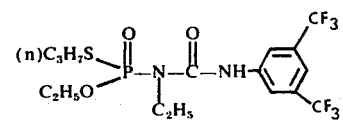

37. Compound according to claim 2 of the formula

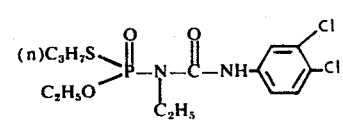

* * * * *